United States Patent [19]

Kieturakis

[11] Patent Number: 5,667,479
[45] Date of Patent: Sep. 16, 1997

[54] METHOD FOR RESECTION OF AN ANATOMIC STRUCTURE

[75] Inventor: Maciej J. Kieturakis, San Carlos, Calif.

[73] Assignee: Archimedes Surgical, Inc., Menlo Park, Calif.

[21] Appl. No.: 316,290

[22] Filed: Sep. 30, 1994

Related U.S. Application Data

[63] Continuation-in-part of Ser. No. 255,273, Jun. 1, 1994, Pat. No. 5,569,183.

[51] Int. Cl.⁶ .................................................. A61B 1/32
[52] U.S. Cl. ............... 600/207; 600/204; 600/215; 604/49; 606/192
[58] Field of Search .................. 600/204, 207, 600/208, 215; 604/49, 156; 606/192; 602/13; 128/DIG. 20

[56] References Cited

U.S. PATENT DOCUMENTS

| | | |
|---|---|---|
| 3,831,587 | 8/1974 | Boyd .................................. 600/207 |
| 4,191,191 | 3/1980 | Auburn . |
| 4,535,773 | 8/1985 | Yoon . |
| 4,601,710 | 7/1986 | Moll . |
| 4,654,030 | 3/1987 | Moll et al. . |
| 4,763,662 | 8/1988 | Yokoi .................................. 128/660 |
| 4,770,163 | 9/1988 | Ono et al. ............................. 128/6 |
| 5,041,089 | 8/1991 | Mueller et al. ........................ 604/96 |
| 5,116,353 | 5/1992 | Green . |
| 5,147,316 | 9/1992 | Castillenti . |
| 5,147,376 | 9/1992 | Pianetti . |
| 5,188,630 | 2/1993 | Christoudias ........................ 606/191 |
| 5,203,773 | 4/1993 | Green . |
| 5,209,736 | 5/1993 | Stephens et al. . |
| 5,224,952 | 7/1993 | Deniega et al. . |
| 5,226,890 | 7/1993 | Ianniruberto et al. . |
| 5,232,451 | 8/1993 | Freitas et al. . |
| 5,258,003 | 11/1993 | Ciaglia et al. . |
| 5,271,380 | 12/1993 | Riek et al. . |
| 5,279,567 | 1/1994 | Ciaglia et al. . |
| 5,334,185 | 8/1994 | Giesy et al. ......................... 604/164 |
| 5,336,252 | 8/1994 | Cohen ................................ 607/119 |
| 5,346,504 | 9/1994 | Ortiz et al. ......................... 606/192 |
| 5,395,030 | 3/1995 | Kuramoto et al. .................... 227/179 |
| 5,468,248 | 11/1995 | Chin et al. .......................... 600/207 |

*Primary Examiner*—Beverly M. Flanagan
*Attorney, Agent, or Firm*—Skjerven, Morrill, MacPherson, Franklin & Friel; Norman R. Klivans

[57] ABSTRACT

A surgical instrument and method for facilitating the resection of an anatomic structure in a minimally invasive procedure. The resection instrument includes an inflatable enveloping sleeve member that has an inflation chamber lying between an outer sleeve and an inner sleeve thus providing an inflatable chamber that surrounds an "organ lumen" extending along the member's longitudinal axis. The enveloping member typically is of non-elastomeric sheet material and in the collapsed state is folded and stored in the instrument's handle by turning both the inner and lumen sleeves "inside-out". The instrument is disposed proximate to the anatomic structure to be resected and the enveloping member is inflated. As the inflation chamber is inflated, the enveloping member deploys distally turning itself "right-side-out" and is capable of circumferentially enveloping the anatomic structure (or portion thereof) thus progressively capturing the structure within the organ lumen. Thus, the enveloping member bluntly dissects connective tissues in 360° surrounding the structure creating an anatomic space. Thereafter, the anatomic structure may be divided beyond the distal end of the enveloping member and the instrument and resected structure withdrawn.

29 Claims, 8 Drawing Sheets

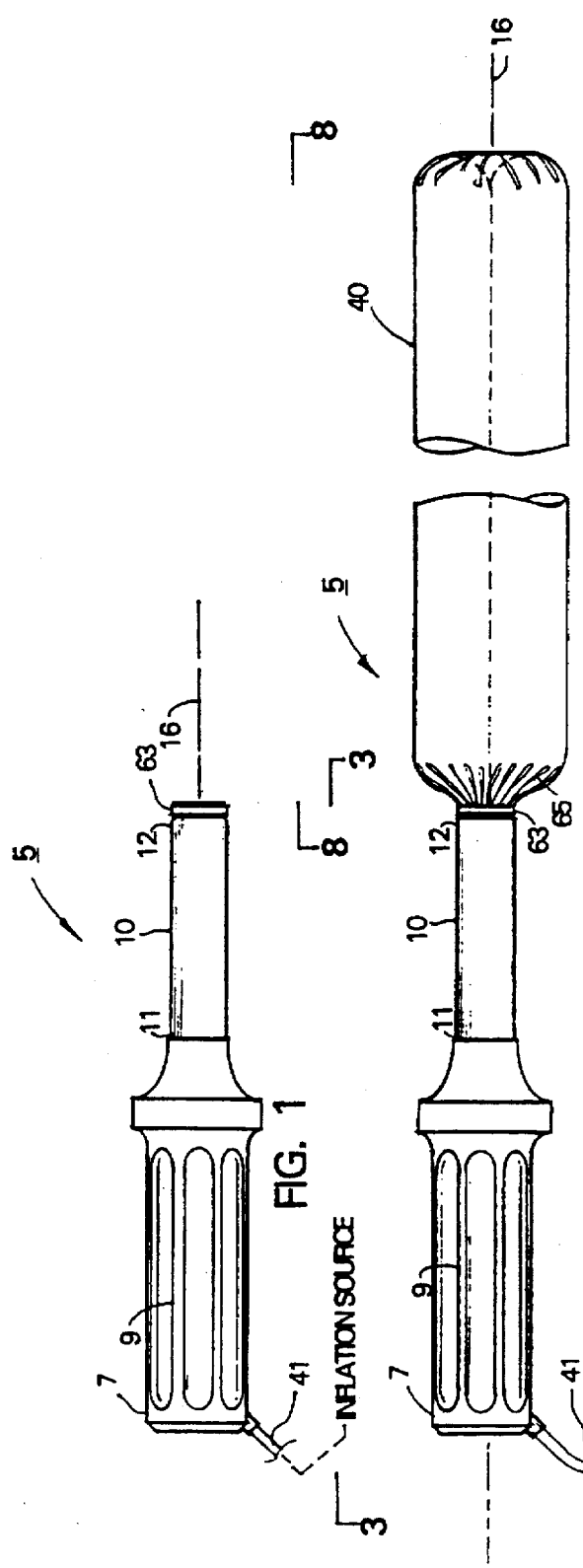

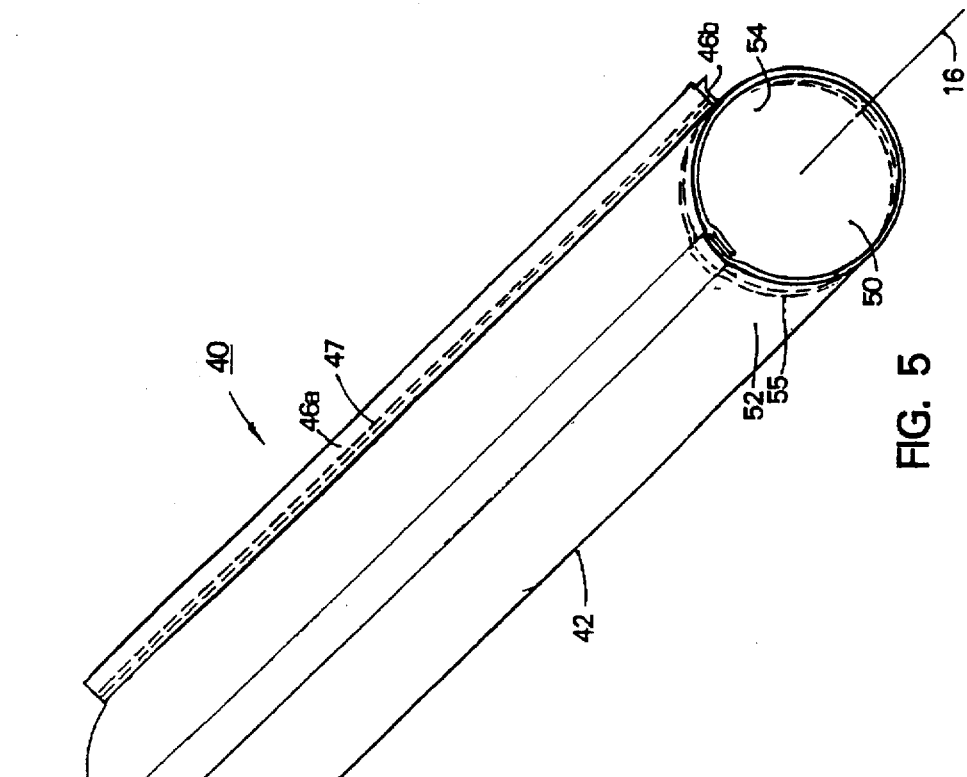
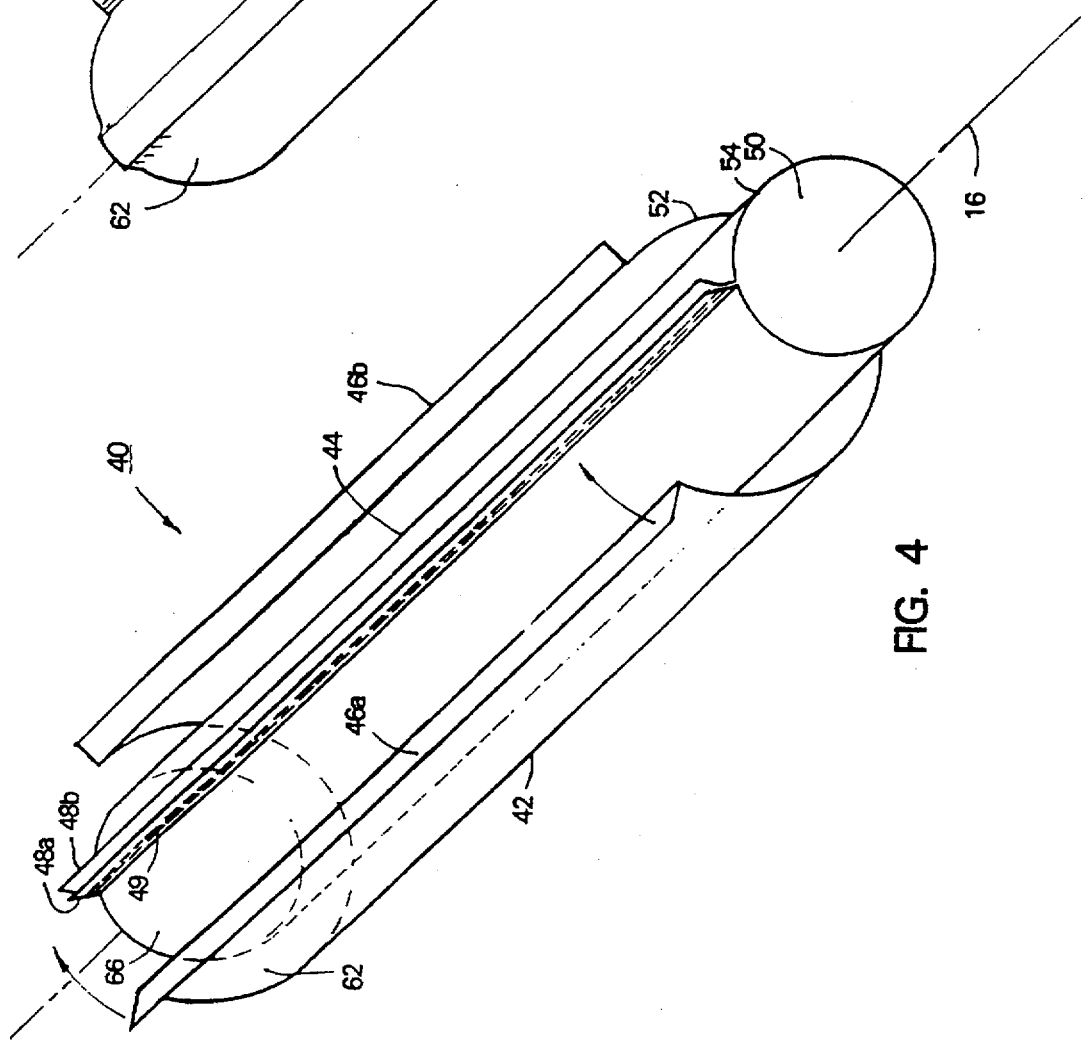

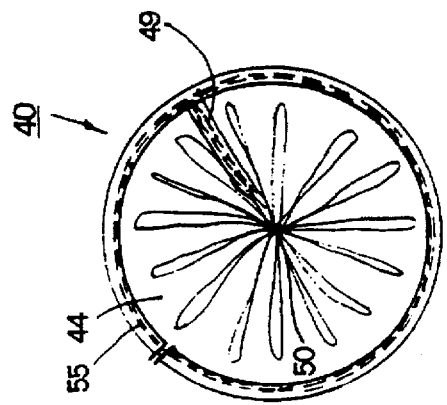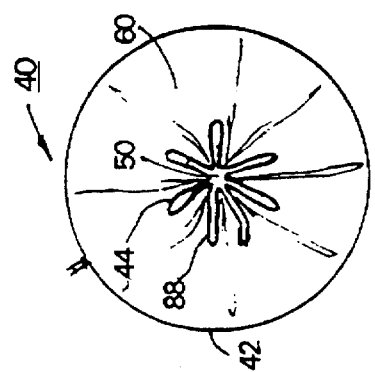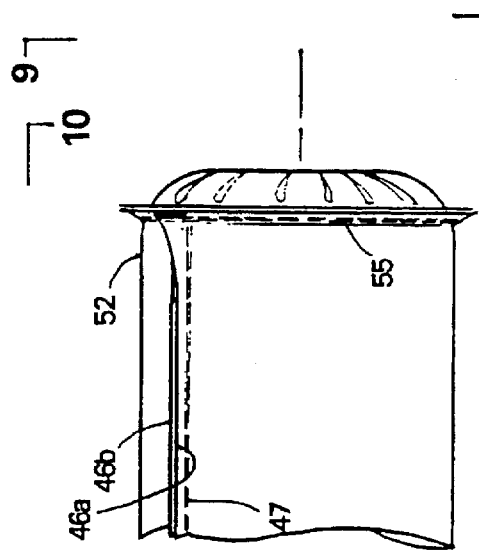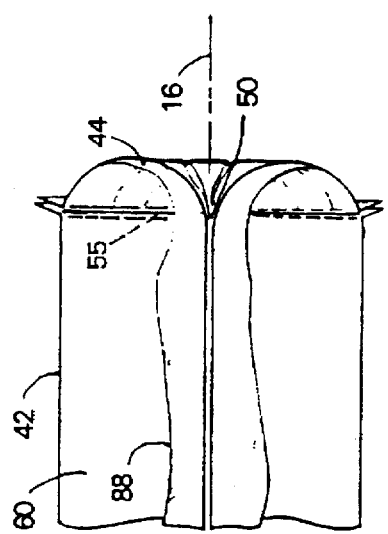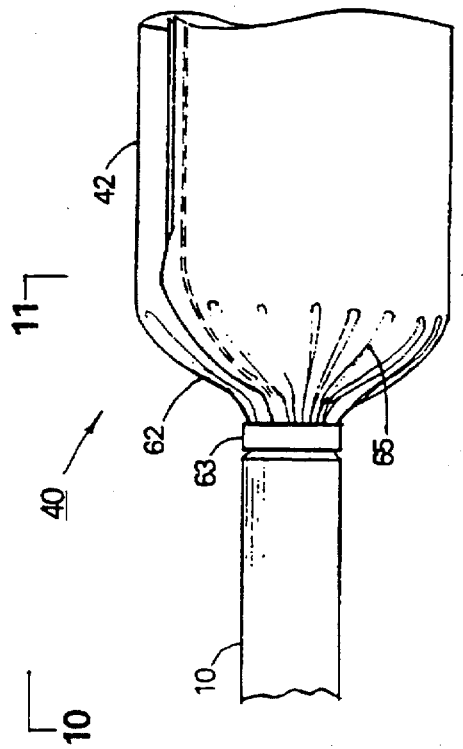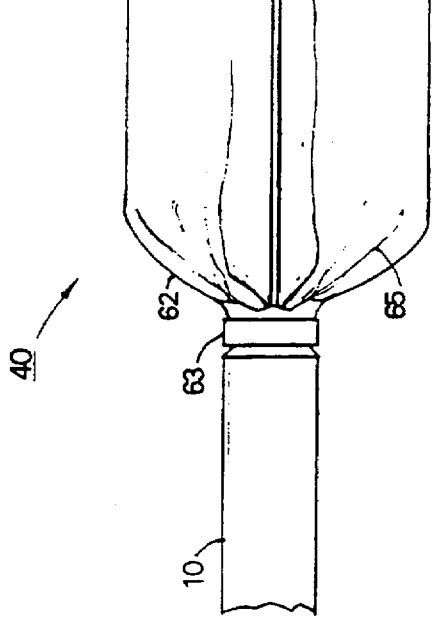

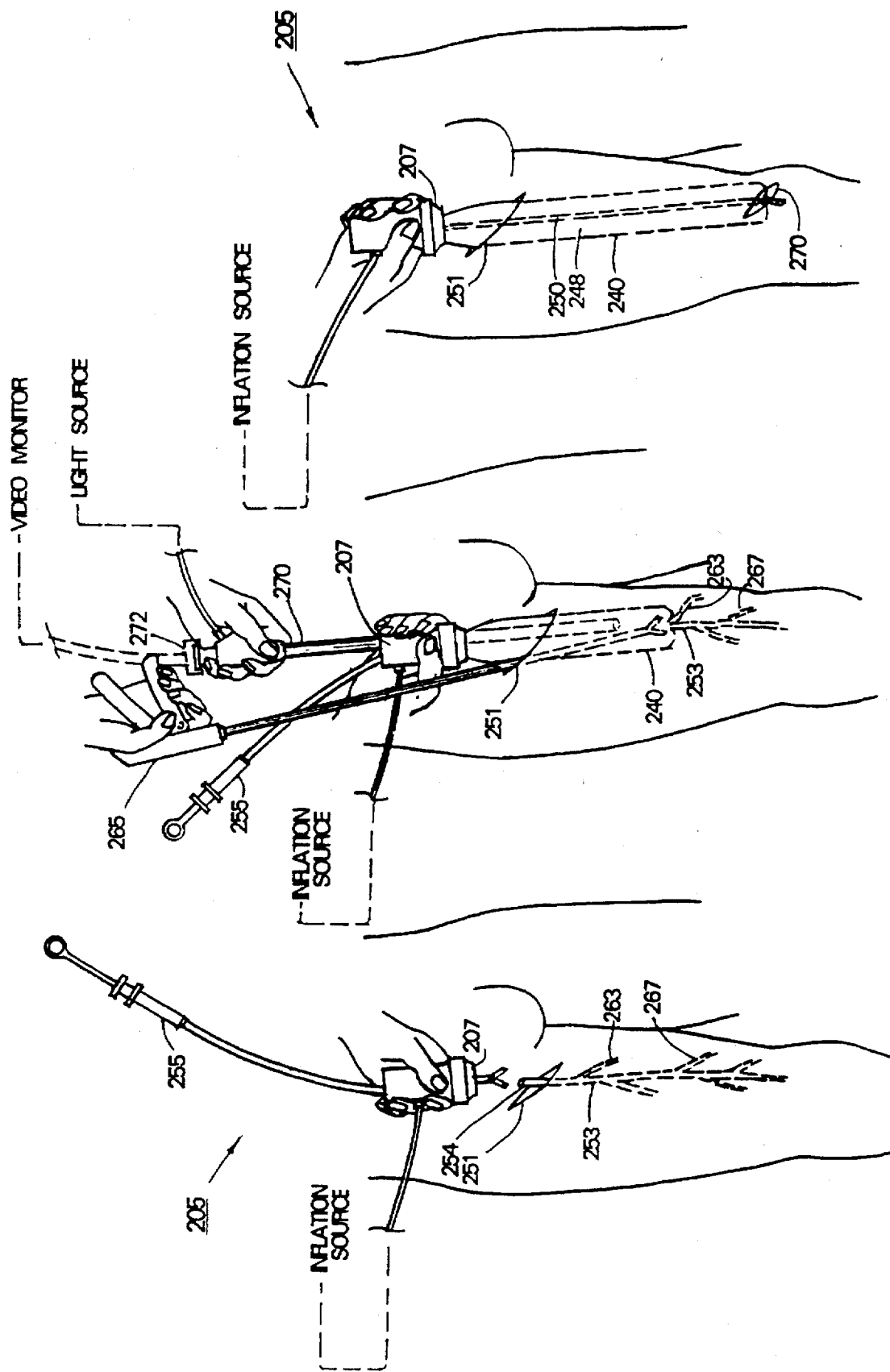

METHOD FOR RESECTION OF AN ANATOMIC STRUCTURE

CROSS-REFERENCE TO RELATED APPLICATIONS

This application is a continuation-in-part of commonly invented application "Instrument and Method for Performing Surgery Around a Viewing Space in the Interior of the Body" filed Jun. 1, 1994, Ser. No. 08/255,273, now U.S. Pat. No. 5,569,183. This application also is related to a co-pending and commonly invented application which is incorporated herein by reference: "Surgical Instrument and Method for Intraluminal Retraction of an Anatomic Structure" filed Aug. 9, 1994, Ser. No. allowed.

BACKGROUND OF THE INVENTION

1. Field of the Invention

This invention relates to surgical instrumentation and more particularly to an instrument and "minimally invasive" method utilizing an inflatable envelope to bluntly dissect connective tissues that adhere between an organ and surrounding tissue preparatory to resection of the organ. The above-mentioned parent application Ser. No. 08/255,273 discloses an inflatable envelope for bluntly dissecting tissue and creating an anatomic space along a natural anatomic plane and a method for fiberoptically viewing and for performing a surgery around the surface of the inflated envelope. The method of the present application also provides for fiberoptically viewing around the exterior of the inflatable envelope and for performing a sharp dissection around the inflated envelope to facilitate the resection procedure.

2. Description of the Prior Art

Preparatory to resection (removal) of part or all of an organ or anatomic structure, surgeons in the past have used sharp-tipped instruments (e.g., a scalpel) to sharply dissect connective tissues that typically adhere between the organ and surrounding tissues to mobilize the organ. Surgeons also have utilized blunt instruments (e.g., a grasper or the human fingers) to bluntly dissect connective tissues around an organ to mobilize the organ.

An illustrative example of a resection procedure in which mobilization of the organ is difficult is a transhiatal esophagectomy. It typically is necessary to divide the esophagus in the throat and in the region of the gastroesophageal junction. To mobilize the esophagus, the surgeon reaches with his fingers blindly into the thoracic cavity from incisions in the throat and abdomen to bluntly dissect connective tissues around the esophagus. Such blind dissection with the fingers is undesirable. On occasion, it may be necessary to open the thoracic cavity which also is undesirable.

Another example of a resection procedure in which minimally invasive procedures are not practiced is the harvesting of a saphenous vein associated with a heart bypass procedure. Under current practice, an open surgical approach exposes the entire length of the vein in the thigh, requiring an incision 12 inches or more in length. Such an open procedure leaves undesirable scarring, is time-consuming and requires lengthy postoperative recuperation.

Other anatomic structures that may be candidates for resection vary widely. Resection of organs or parts of organs with the abdominal cavity is often necessary and the surgeon typically mobilizes such organs with his fingers in an open procedure. Under current practice, it is difficult to accomplish such abdominal resection procedures in a "minimally invasive" or endoscopic approach, in part, because of difficulties in mobilizing the organ. For this reason, an invention to facilitate the mobilization of the colon in a colectomy (colon resection) is disclosed in the above-referenced co-pending application: "Surgical Instrument and Method for Intraluminal Retraction of an Anatomic Structure" filed Aug. 9, 1994, Ser. No.

The above-described procedures have in common the difficulty of mobilizing and resecting an anatomic structure by any means other than an open surgical procedure. There is therefore a need for new instruments and methods for dissecting tissues that surround an anatomic structure to mobilize the structure preparatory to resection. More particularly, there is a need for a less invasive surgical approach for mobilizing an esophagus in a transhiatal esophagectomy, for mobilizing and resecting a saphenous vein and for mobilizing and resecting organs in an insufflated workspace.

SUMMARY OF THE INVENTION

In general, the instrument of the present invention includes an inflatable "enveloping sleeve member" that is deployable from the distal end of a handle. The enveloping sleeve member has an internal inflation chamber that lies between an outer sleeve and an inner sleeve thus providing an inflatable chamber that surrounds an "organ lumen" that extends along the enveloping member's longitudinal axis.

The enveloping sleeve member typically is made of non-elastomeric sheet material and in the collapsed state is folded and stored in the instrument's handle by turning both the outer and inner sleeves "inside-out". As the inflation chamber between the outer sleeve and inner sleeve is inflated, the member deploys by projecting distally outward from the handle thus turning itself "right-side" out. As the enveloping member deploys right-side out, it is capable of circumferentially wrapping itself around an organ (or portion thereof) thus leaving the organ isolated and captured within the organ lumen. An accessory instrument (e.g., a grasper) is introduced through a central bore in the handle to grip and position the organ as it is isolated within the organ lumen. As the enveloping sleeve member progressively envelops an organ, the distal deployment of the enveloping member bluntly dissects connective tissues in 360° surrounding the organ that adhere between the organ and surrounding tissue.

As inflation pressures in the inflation chamber are increased, the organ lumen is compressed radially inward to provide a firm grip around the organ. The grip on the organ is sufficient to allow the surgeon to reposition or retract the organ by manipulation of the handle to facilitate the resection procedure.

In general, the present invention provides an instrument and method for dissecting connective tissues that surround an anatomic structure. The present invention also provides an instrument and method for dissecting such connective tissues without the use of sharp dissecting instruments. The present invention also provides an instrument for dissecting tissue and creating an anatomic space in 360° around the structure with an inflatable enveloping member. The present invention also provides an instrument and method that applies substantially perpendicular forces along a natural anatomic plane to less traumatically dissect and create an anatomic space.

The present invention provides an instrument and method that dissects connective tissues in 360° around an anatomic structure organ in a single step utilizing a single instrument.

The present invention provides an instrument and method that accommodates an endoscope disposed within the inflation chamber of the inflatable enveloping member for viewing structures exterior to the transparent-walled enveloping member. The present invention also provides a method for performing a surgical procedure in the interface between the enveloping member and surrounding tissue under endoscopic vision. The present invention provides an instrument and method that captures a resected anatomic structure within a lumen in an inflatable enveloping member to retract the anatomic structure to facilitate a resection.

Additional advantages and features of the present invention appear in the following description.

DESCRIPTION OF THE DRAWINGS

FIG. 1 is an elevational view of a resection instrument in accordance with the present invention.

FIG. 2 is an elevational view of the resection instrument of FIG. 1 with the enveloping sleeve member in a deployed configuration.

FIG. 3 is a longitudinal sectional view of the instrument of FIG. 2 taken along line 3—3 of FIG. 2.

FIG. 4 is an axionometric view of a disassembled enveloping sleeve member.

FIG. 5 is another axionometric view of the enveloping sleeve member of FIG. 4 in a partially assembled state.

FIG. 8 is an elevational view of the enveloping sleeve member of FIG. 4 in an inflated state taken along line 8—8 of FIG. 2.

FIG. 9 is an elevational view of the enveloping sleeve member of FIG. 8 taken along line 9—9 of FIG. 8.

FIG. 10 is a longitudinal partial sectional view of the enveloping sleeve member of FIG. 8 taken along line 10—10 of FIG. 8.

FIG. 11 is an elevational view of the enveloping sleeve member of FIG. 8 taken along line 11—11 of FIG. 8.

FIGS. 15A–15D are illustrations of a patient's lower body showing the manner in which the instrument of FIG. 14 is utilized to resect a saphenous vein.

DETAILED DESCRIPTION OF THE INVENTION

Figure 7:
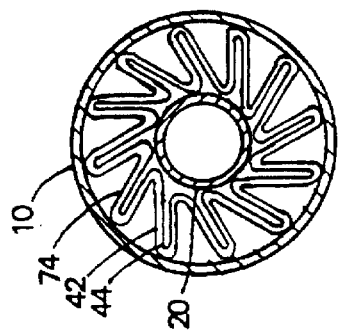
FIG. 7 is a transverse sectional illustrations in not-to-scale format representing a manner of radially folding the enveloping sleeve member of FIG. 5.

By way of example, FIGS. 1–3 illustrate resection instrument 5 in accordance with the present invention that is suitable for mobilizing the esophagus in a transhiatal esophagectomy. FIG. 1 shows plastic handle 7 with grooves 9 to facilitate gripping with the human hand. Handle 7 is coupled to outer guide tube 10 which has proximal and distal ends respectively 11 and 12, and is fabricated from a thin-wall metal, plastic or glass fiber with bore 15 extending therethrough along axis 16. Instrument guide tube 20 having proximal and distal ends respectively 21 and 22, is a thin-wall tube made of metal, plastic or glass fiber with bore 25 extending therethrough along axis 16. It should be appreciated that outer guide tube 10 may be any suitable diameter from less than 10 mm. to more than 40 mm. and be within the scope of the present invention. Referring to FIG. 3, instrument guide tube 20 has a 5 mm. inside diameter to accommodate the introduction of a standard 5 mm. diameter endoscopic accessory instrument (e.g., a grasper). The proximal region of instrument guide tube 20 is fixed in handle 7 along axis 16.

Referring to FIG. 3, handle 7 and associated outer guide tube 10 define internal storage chamber 30 that surrounds the exterior of instrument tube 20 for storing enveloping sleeve 40 in an uninflated state. In FIG. 3, enveloping sleeve member 40 is shown in the uninflated state prior to being folded and packed in storage chamber 30. Inflation tube 41 is sealed in the proximal end of handle 7 and communicates with storage chamber 30 which is fluid-tight.

Referring now to FIGS. 4–5, enveloping sleeve member 40 is fabricated typically from transparent thin plastic sheets such as Mylar or PET-E®. The plastic sheets are formed into outer sleeve 42 and lumen sleeve 44 extending around axis 16. Although outer sleeve 42 and lumen sleeve 44 are illustrated as being of nonelastomeric sheet material, lumen sleeve 44 only may be made from elastomeric material such as latex. The circumferential dimensions of sleeves 42 and 44 are similar providing a diameter of approximately 40 mm. to 50 mm. (not limiting) to facilitate a transhiatal esophagectomy. The longitudinal dimensions of lumen sleeve 44 exceeds the similar dimension of outer sleeve 42 but such dimensional relationships are not limiting. The overall length of the enveloping sleeve for an esophagectomy is approximately 400 mm. (not limiting).

Referring to FIG. 5, longitudinal edge portions 46a and 46b of outer sleeve 42 are sealed and joined by heat seal 47. Similarly, longitudinal edge portions 48a and 48b of lumen sleeve 44 are sealed and joined by heat seal 49 (see FIG. 4). Lumen sleeve 44 thus defines an axial-extending interior organ lumen 50 that is capable of enveloping and isolating an organ. FIG. 5 illustrates the distal ends, 52 and 54, of outer sleeve 42 and lumen sleeve 44 respectively joined by heat seal 55.

Referring back to FIG. 3, the space between outer sleeve 42 and lumen sleeve 44 is inflation chamber 60 and communicates with storage chamber 30. FIG. 3 depicts the proximal end 62 of outer sleeve 42 sealed to the distal end 12 of guide tube 10 with adhesives and metal sealing ring 63. In order to taper outer sleeve 42 to the dimension of guide tube 10, a plurality of tapering folds 65 are formed. Similarly, the proximal end 66 of lumen sleeve 44 has tapering folds 67 and is sealed to distal end 22 of instrument tube 20 with adhesives and metal sealing ring 68.

Figure 6A:
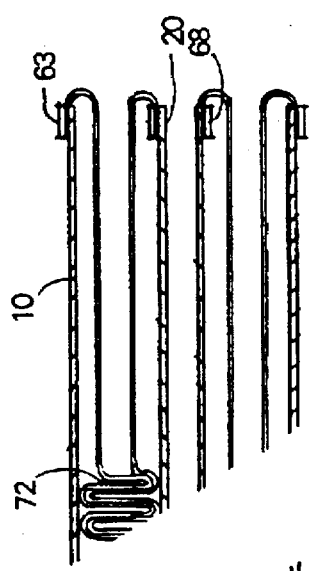
FIGS. 6A–6C are longitudinal sectional illustrations in not-to-scale format representing alternative manners of folding the enveloping sleeve member of FIG. 5.
Figure 6B:
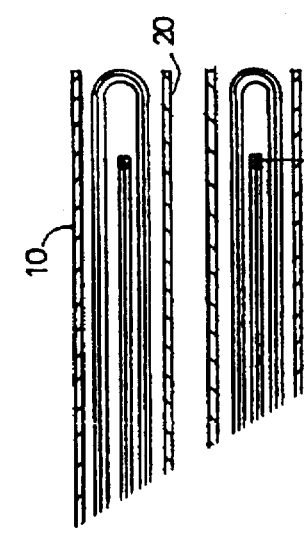
Figure 6C:
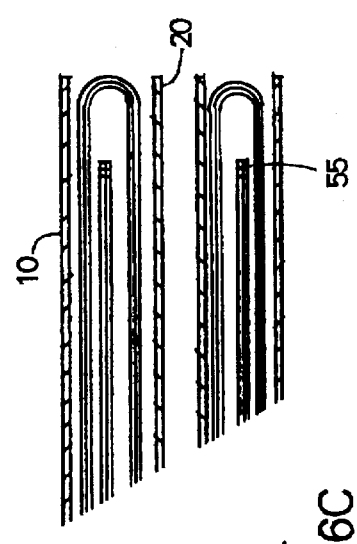

FIGS. 6A–6C are not-to-scale sectional illustrations of alternate ways in which enveloping sleeve member 40 may be folded to be packed into storage chamber 30. The folding alternatives provide a different manner of deployment or unfolding, each of which may carry an advantage for a particular resection procedure. For an esphagectomy and most other resections, it is preferable to fold enveloping sleeve member 40 as depicted in FIG. 6A. In FIG. 6A, the enveloping member is turned "inside-out" within storage chamber 30. To fit the enveloping member within storage chamber 30, it is necessary to have additional "accordion" folds 72 as well as "radial" folds 74 (see transverse sectional view FIG. 7).

FIGS. 6B and 6C depict alternative folding patterns in which enveloping sleeve 40 is attached within the proximal portion of outer guide tube 10 and instrument guide tube 20. In FIG. 6B, the sleeve is folded or rolled outwardly over instrument tube 20 in the longitudinal direction. In FIG. 6C, the sleeve is folded or rolled inwardly within guide tube 10. Both folding patterns of FIGS. 6B and 6C also may require longitudinal accordion folds and radial folds as described above (not shown) to fit within storage chamber 30.

A mechanism is provided for introducing an inflation medium, preferably $CO_2$ gas or saline solution, into chamber 60. Referring to FIGS. 1–3, the proximal end of inflation tube 41 receives an inflation source, for example, the inflation tube may be connected to a syringe holding saline solution. Alternatively, a conventional gas inflation source found in an operating room is suitable.

FIGS. 8–11 depict respectively plan and sectional views of enveloping sleeve member 40 after being deployed by the introduction of an inflation medium into inflation chamber 60. In FIGS. 8–9, the inflation medium has expanded chamber 60 to compress the walls of lumen sleeve 44 radially inward to axis 16 such that organ lumen 50 has no radial dimension. The views of FIGS. 9 and 11 depict resultant irregular longitudinal folds 88 that develop as lumen sleeve 44 is compressed radially inward to axis 16. More particularly, as chamber 60 is inflated, the non-elastomeric plastic sheet material of outer sleeve 42 expands to its maximum diameter and thereafter inflation pressure is directed radially inward on lumen sleeve 44 toward axis 16. As described above, the lumen sleeve 44 only may be fabricated of elastomeric material (e.g., latex or silicon) and such material may have a gripping surface (not shown) such as a sticky, textured or ribbed surface to better grip an anatomic structure captured within lumen 50.

Operation and use of instrument 5 shown in FIG. 1 in performing a method in accordance with the present invention to facilitate a transhiatal esphagectomy is described briefly with reference to FIGS. 12A–12E. Assume the patient is conventionally prepared with a suitable anesthesia.

Figure 12A:
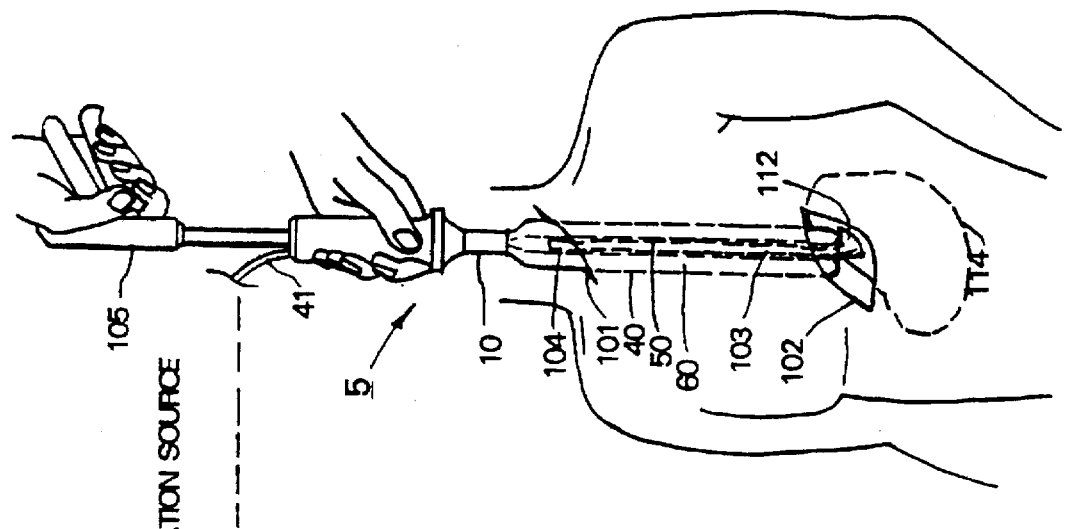
FIGS. 12A–12C are illustrations of a patient's upper body showing the manner in which the instrument of FIGS. 1–3 is utilized to perform an esophagectomy.

Referring to FIG. 12A, the surgeon makes incision 101 in the region of the patient's throat and incision 102 in the patient's abdomen. The surgeon then divides the esophagus 103 at a suitable location in the throat within incision 101 to provide proximal end 104 of the now-divided portion of the esophagus.

Figure 12B:
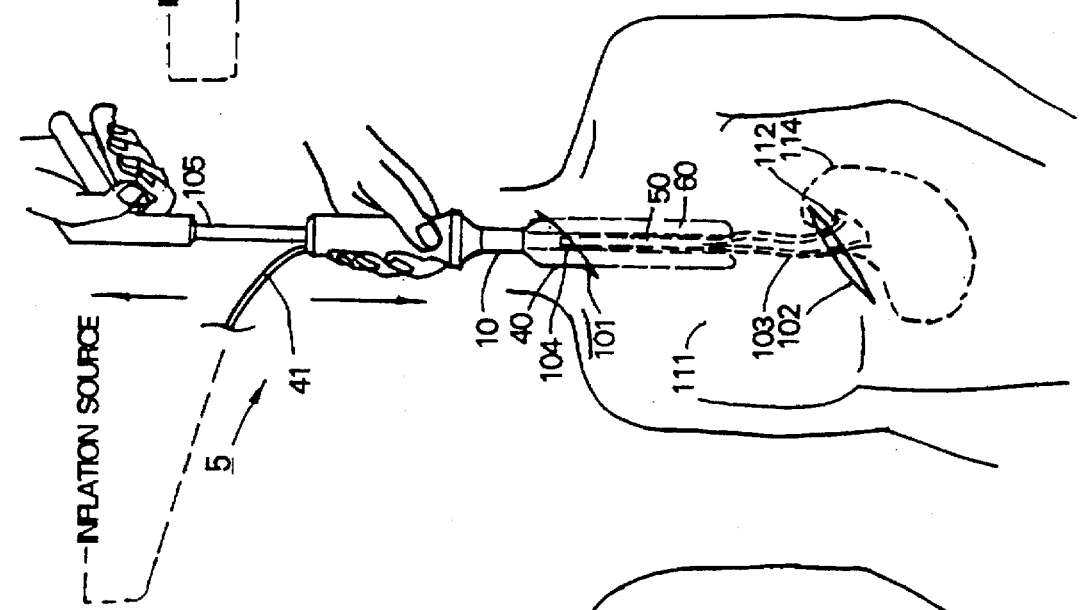
Figure 12C:
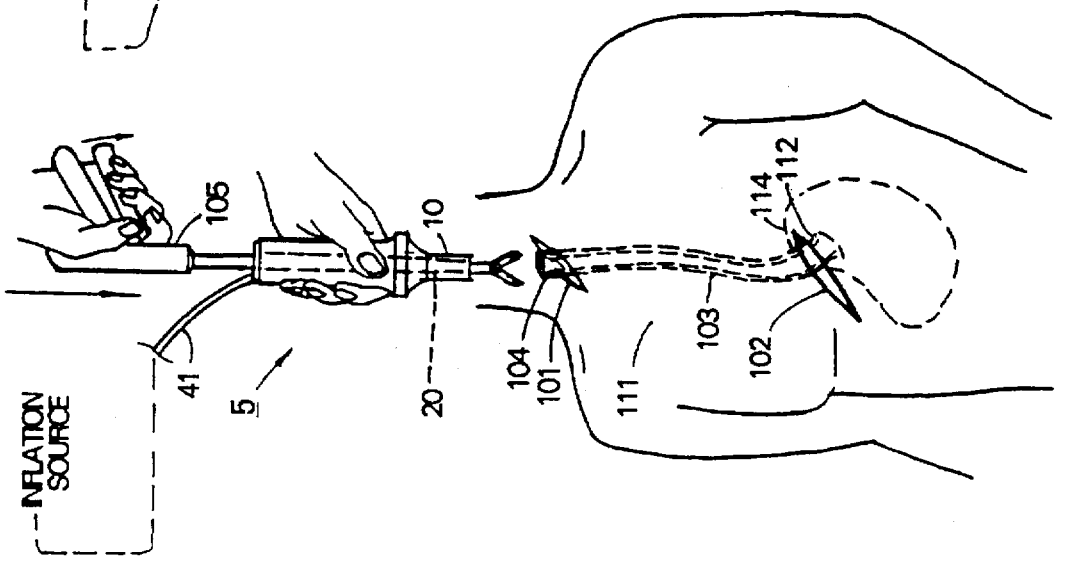

The surgeon then introduces accessory instrument 105 (e.g., a 5 mm. grasper) through instrument guide tube 20 of instrument 5. The surgeon grasps divided end 104 of the esophagus and holds it in position longitudinally. Referring to FIG. 12B, instrument 5 is then slid slightly distally over the shaft of grasper 105 until proximal end 104 of esophagus 103 is close to the distal end of outer guide tube 10. The surgeon then instructs an assistant to introduce an inflation medium into instrument 5 thereby causing enveloping sleeve member 40 to deploy distally outward from the distal end of outer guide tube 10. In an esophagectomy, a syringe filled with saline solution is the preferred inflation source (not shown). As sleeve member 40 inflates, it surrounds and progressively envelops esophagus 103 within organ lumen 50 as the sleeve unfolds in 360° and moves distally. The progressive deployment of enveloping sleeve member 40 disrupts and dissects connective tissues that surround esophagus 103 within the thoracic cavity 111. Referring to FIG. 12C, as the distal end of the enveloping sleeve 40 approaches the gastroesophageal (GE) junction 112 above stomach 114, the surgeon may view sleeve 40 through incision 102. The surgeon then divides esophagus 103 in the region of the GE-junction 112 thus leaving the resected portion of the esophagus compressed within organ lumen 50 of sleeve member 40. The surgeon then withdraws sleeve member 40 proximally from incision 101 together with the resected esophagus 103 (not shown). Sleeve 40 is preferably deflated partially or completely before it is withdrawn proximally, but withdrawal of the sleeve in an inflated condition also is possible.

Figure 12D:
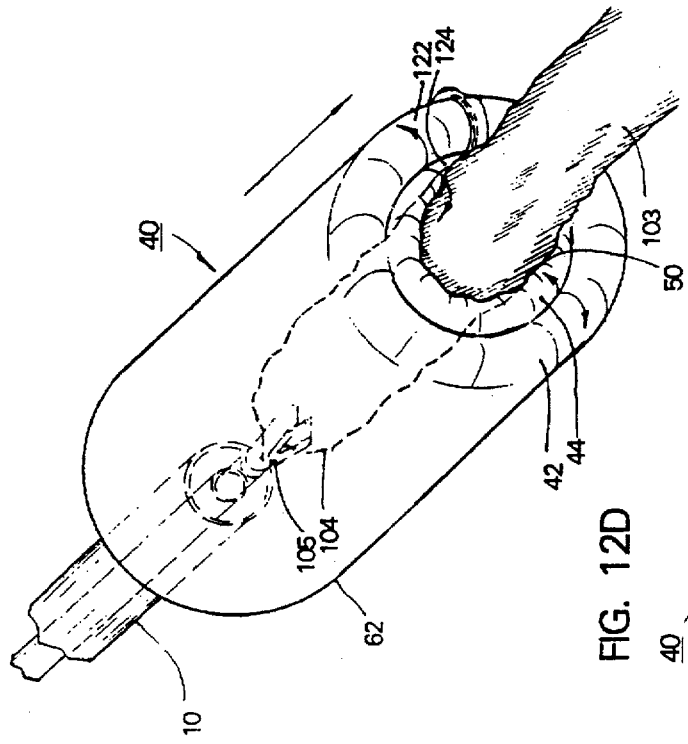
FIGS. 12D–12E are axionometric and sectional views of the enveloping sleeve member in the process of deploying as it envelops the esophagus.
Figure 12E:
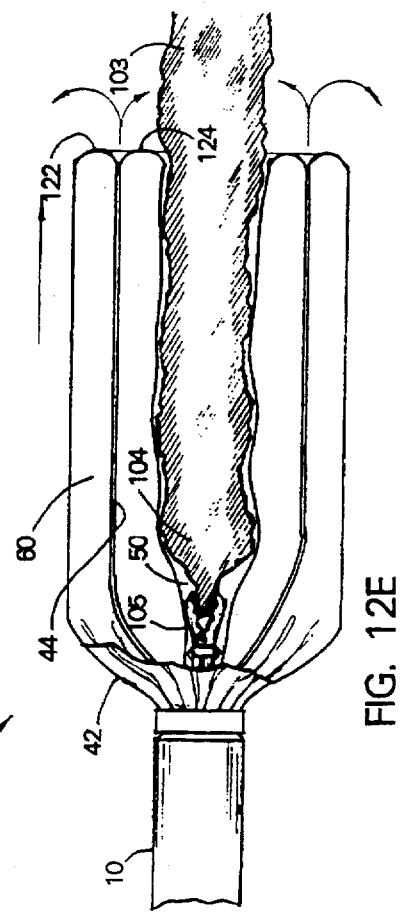

Of particular interest regarding the present invention is the application of blunt dissecting forces caused by enveloping sleeve member 40 turning itself "right side-out" from the "inside-out" stored configuration. Referring to FIGS. 12D–12E, which are enlarged axionometric and sectional views similar to FIG. 12B, the outer surface 122 of outer sleeve 42 progressively unfolds and unrolls within surrounding tissues thus causing no friction between surface 122 and such surrounding tissues. Likewise, the outer surface 124 of lumen sleeve 44 progressively unfolds or unrolls over esophagus 103 which is disposed within lumen 50 thus causing no friction between surface 124 and the esophagus. This manner of progressive distal unfolding of enveloping sleeve member 40 in 360° around esophagus 103 causes disruptive forces (blunt dissection forces) that are substantially perpendicular to axis 16 and that stretch and finally dissect connective tissues.

FIGS. 6B and 6C above depicted alternative folding patterns that may be useful in certain dissections. The folding patterns FIGS. 6B and 6C deploy by unrolling distally and may be utilized to create dissection forces that are partially longitudinal as the surfaces of the enveloping member cause friction between the enveloping member and surrounding tissue as well as the anatomic structure being resected.

The mobilization of esophagus 103 in thoracic cavity 111 may be performed blindly as illustrated in FIGS. 12A–12C. It should be appreciated that an endoscope (along with other accessory instruments) may be introduced through either incision 101 or 102 and slid over outer surface of an inflated enveloping sleeve 40 to perform a surgical procedure, wherein the term surgical procedure includes viewing and diagnosing as well as dissecting tissue. Such surgical procedures performed around the surface of an inflatable sleeve under endoscopic vision are similar to the methods disclosed in the co-pending parent application "Instrument and Method for Performing Surgery Around a Viewing Space in the Interior of the Body" U.S. Pat. No. 5,569,183 issued Oct. 29, 1996 referenced above.

Figure 13A:
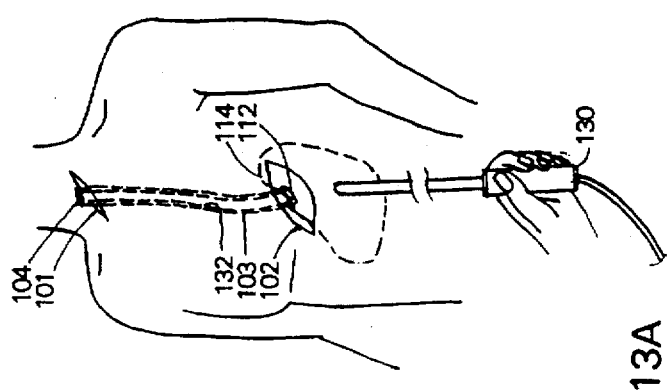
FIGS. 13A–13B are illustrations of a variation of the method of FIGS. 12A–12C in performing an esophagectomy.
Figure 13B:
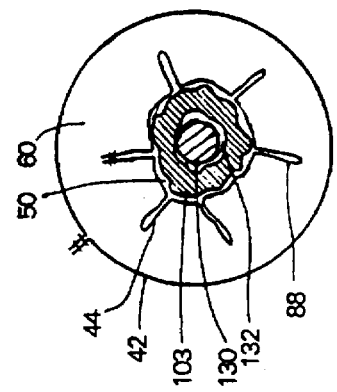

FIGS. 13A and 13B illustrate a variation on the method of performing the esophagectomy described above. FIG. 13A depicts the surgeon prepared to introduce a "variform intraluminal retractor" 130 into and through esophageal passageway 132 from incision 102 to provide rigidity to esophagus 103 before utilizing instrument 5 to mobilize the esophagus in the manner described above. The term "variform intraluminal retractor" herein refers to the invention disclosed in co-pending application "Surgical Instrument and Method for Intraluminal Retraction of Anatomic Structure" U.S. Pat. No. 5,558,665, issued Sep. 24, 1996. The introduction of various intraluminal retractor 130 entirely through esophagus 103 and the maintenance of the variform retractor in a rigid configuration eliminates the need to use grasper 105 to position the esophagus as enveloping sleeve member 40 is first deployed over the proximal end 104 of esophagus 103. The enveloping member also will tend to easily follow the rigidified esophagus, even if the esophagus is somewhat articulated by retractor 130. FIG. 13B depicts a transverse sectional view of esophagus 103 with variform intraluminal member 130 (phantom view) in esophageal passageway 132.

Another embodiment of resection instrument 205 incorporating the present invention is shown in FIGS. 14 and 15A–15D. Instrument 205 is adapted for harvesting a saphenous vein and differs from instrument 5 described above principally in that instrument 205 is capable of accommodating an endoscope within the inflation chamber of the transparent enveloping sleeve member to view around the surface of the sleeve member as it deploys. Such endoscopic viewing is required in a "minimally invasive" approach to resecting and recovering a saphenous vein because several branch veins must be clipped (sharply dissected) with an accessory instrument.

Figure 14:
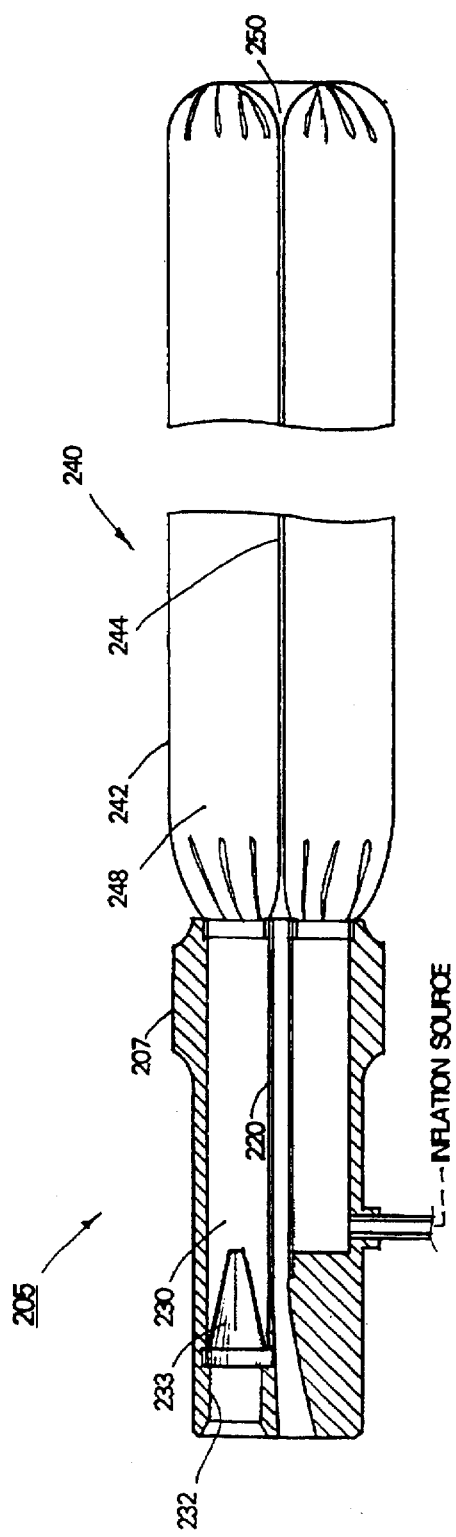
FIG. 14 is an alternative embodiment of a resection instrument of the present invention in a longitudinal partial sectional view.

Referring to FIG. 14, handle 207 includes central 5 mm. diameter instrument tube 220. Storage chamber 230 surrounds instrument tube 220. An endoscope may be introduced through port 232 in the proximal end of handle 207 and through conventional duck-bill silicon seal 233 into chamber 230. The transverse dimension of at least one side of the chamber 30 is capable of accommodating the introduction therethrough of an endoscope, such as a standard 10 mm. scope (not limiting). Inflation port 231 communicates with storage chamber 230. Enveloping sleeve member 240 has an diameter of approximately 30 mm. to 50 mm. and a length of approximately 300 mm. to 400 mm. (not limiting). As previously described, the proximal ends of outer sleeve 242 and lumen sleeve 244 are fixed to the handle 207 and instrument tube 220, respectively. Organ lumen 250 is shown in FIG. 14 with the sleeve member in an inflated configuration. Inflation chamber 248 communicates with fluid-tight storage chamber 230.

Figure 15D:
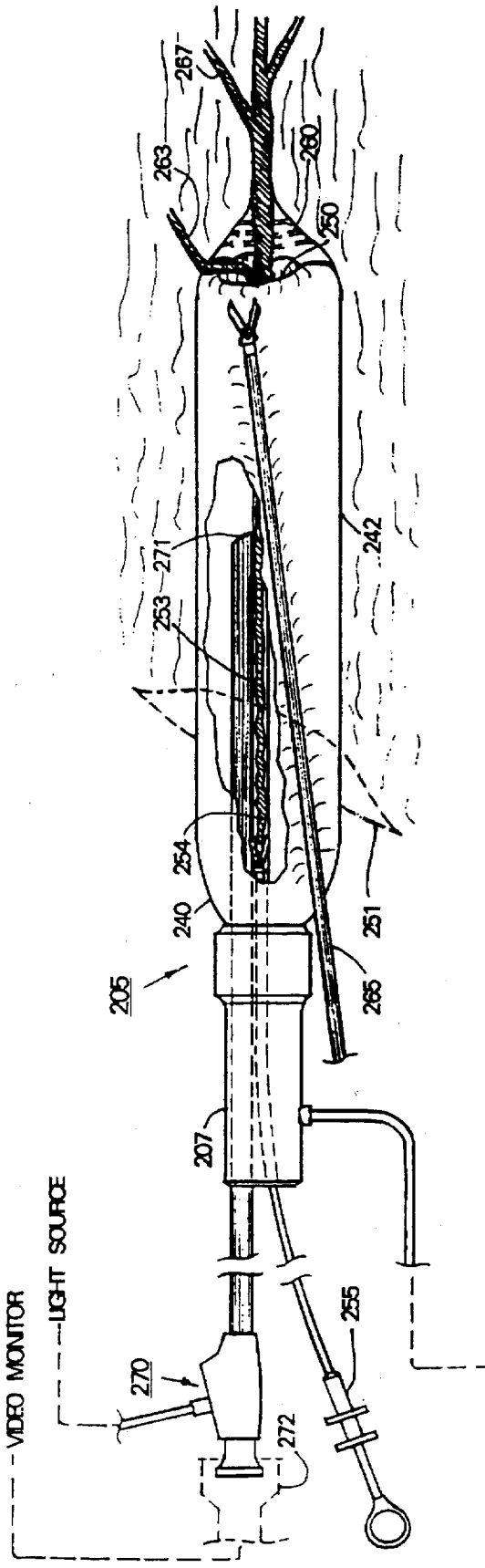

Operation and use of instrument 205 shown in FIG. 14 in performing the method in accordance with the present invention to harvest a saphenous vein is described briefly with reference to FIGS. 15A–15D. The patient is conventionally prepared with a suitable anesthesia. Referring to FIG. 15A, the surgeon makes incision 251 in the region of the patient's thigh and then divides the saphenous vein 253 at a suitable location within the incision to provide proximal end 254 of the now-divided vein 253.

The surgeon then introduces accessory instrument 255 (e.g., a 3 mm. diameter flexible grasper with locking jaws) through instrument guide tube 220 of instrument 205. The surgeon grasps divided end 254 of vein 233 and holds it in position. Referring to FIG. 15B, instrument 5 is then slid slightly distally over the flexible shaft of grasper 255 until end 254 of vein 253 is close to the distal end of handle 207. The surgeon then instructs an assistant to introduce an inflation medium into instrument 205 thereby causing enveloping sleeve member 240 to deploy distally from handle 207. For a saphenous vein resection, a conventional operating room $CO_2$ gas source is the preferred inflation source (not shown). The assistant also uses one hand to stabilize instrument 205. As enveloping sleeve member 240 inflates, it progressively isolates vein 253 within organ lumen 250 as the sleeve unfolds in 360° thus dissecting connective tissues 260 that surround vein 253 (see FIG. 15D). It should be noted that prior to deploying enveloping member through incision 251, it may be appropriate to introduce an elongate blunt-tipped probe through incision 251 and thereafter distally along vein 253 (not shown). Such probing with a small diameter blunt probe would begin to dissect a pathway along one side of vein 253 thus making it easier for enveloping member 140 to deploy.

With the assistant handling instrument 205, the surgeon then has two hands free. With one hand, the surgeon introduces endoscope 270 through seal 233 and handle 207 so that its distal lens 271 is within inflation chamber 248 (see FIGS. 15B and 15D). A conventional small video camera 272 is attached to the proximal end of endoscope 270 allowing the surgeon to perform the following procedure by viewing a video monitor (not shown). Still referring to FIGS. 15B and 15D, as the distal end of the enveloping sleeve 240 encounters a branch vein 263, the surgeon manipulates endoscope 260 axially to suitably view branch vein 263. To manipulate endoscope 270 angularly, the surgeon may cock the endoscope within handle 207 and also instruct the assistant to rotate handle 207 of instrument 205 slightly to twist enveloping sleeve member 240 (see FIG. 15D). With his other hand, the surgeon introduces an accessory cutting instrument 265 (e.g., 5 mm. diameter scissors) into incision 251 and along the outer surface of enveloping sleeve member 240 to the location of branch vein 263 and then divides the branch vein. The surgeon then instructs the assistant to further inflate enveloping sleeve 240 until another branch vein 267 is encountered. Branch vein 267 then is divided as in the manner described above.

Of particular interest to the present invention, referring to FIG. 15D, the method of sliding accessory instrument 265 over enveloping member 240 causes the branch veins to be clipped at a radial distance away from the main portion of the vein. The branch veins have a small diameter at a distance away from the main vein. Clipping the branch veins away from the main vein results in relatively little loss of blood and the branch veins do not need to be sutured, thus saving time.

Referring to FIG. 15C, after all branch veins have been divided and a suitable length of vein 253 is within enveloping sleeve 240, the surgeon makes incision 270 and divides vein 253. Instrument 205 with vein 253 captured therein then may be withdrawn proximally, preferable after deflating enveloping sleeve 240 partially or completely.

It should be appreciated that other embodiments of similar resecting instruments may be provided. For example, an instrument (not shown) similar to that of FIG. 1 (instrument 5) may be provided for an endoscopic resection procedure within an insufflated anatomic cavity in which the outer guide tube 10 is elongate, for example 250 mm. to 350 mm. in length, to reach through a cannula assembly. The diameter of such an elongate outer guide tube 10 typically would be 10 mm. to cooperate with a standard 10–11 mm. cannula. The use of such an instrument generally is similar to that described above in FIGS. 12A–12C, with the exception that the resection procedure is performed in an insufflated anatomic cavity under endoscopic vision.

From the foregoing it can be seen that there is provided an instrument and method that allows surgical resections to be accomplished in a "minimally invasive" procedure. It can be seen readily that an inflatable enveloping sleeve member can be manufactured with other special dimensions. Although the instrument and method of the present invention has been described in use for particular resection procedures, the instrument and method may be utilized for the resection of all or a portion of any suitable anatomic structures in the interior of the body.

This disclosure is illustrative and not limiting; further variations will be apparent to one skilled in the art and are intended to fall within the scope of the appended claims.

I claim:

1. A method for facilitating the surgical resection of an anatomic structure with an inflatable enveloping member, comprising the steps of:

providing an instrument comprising an elongate body portion having a proximal end and a distal end and further comprising a collapsed inflatable enveloping member which is extendable from said distal end, said instrument having a lumen extending therethrough;

providing a positioning tool;

creating an incision in the body to provide access to the anatomic structure;

dividing the anatomic structure to provide a proximal end to the anatomic structure;

disposing the enveloping member proximate to the anatomic structure;

introducing said positioning tool into said lumen to secure a position of the proximal portion of the anatomic structure;

inflating the enveloping member so that the enveloping member unfolds around the anatomic structure, thereby isolating the anatomic structure in the lumen;

dividing the anatomic structure beyond a distal end of the enveloping member, thereby capturing the divided anatomic structure in the lumen; and withdrawing the enveloping member proximally with the divided anatomic structure captured therein.

2. The method of claim 1 wherein the inflating step includes deploying the enveloping member distally by turning itself to a right-side-out position from a collapsed inside-out position.

3. The method of claim 1 wherein the inflating step includes deploying the enveloping member distally by unrolling itself over the anatomic structure.

4. The method of claim 1 wherein the inflating step includes creating an anatomic space around the anatomic structure between a first proximal region and second distal region by blunt dissection of tissue around a portion of the anatomic structure between the first region and second region.

5. The method of claim 4 wherein the blunt dissection between said first and second regions includes the application of dissecting forces that are generally perpendicular inwardly-directed around the circumference of said anatomic structure and generally perpendicular outwardly-directed around the circumference of said anatomic structure to create said anatomic space.

6. The method of claim 5 wherein said generally perpendicular inwardly-directed forces on said anatomic structure maintain said anatomic structure in its original anatomic position without displacement in any direction.

7. The method of claim 1 wherein the inflating step is preceded by the instrument from a distal direction into an interior lumen in following steps:

providing an intraluminal retractor;

creating a second incision in the body beyond a distal end of the enveloping member so as to provide access to the anatomic structure and wherein said anatomic structure has an interior lumen; and introducing said intraluminal retractor into said interior lumen in the anatomic structure to secure a position of a proximal portion of the anatomic structure.

8. The method of claim 7 wherein said instrument is an intraluminal retractor of a type that is maintainable in a flexible, semi-rigid or rigid configuration.

9. The method of claim 1 wherein the body portion comprises an inflation chamber and further comprising the step of introducing an endoscope into the inflation chamber and viewing through the enveloping member anatomic structures that are exterior to the enveloping member.

10. The method of claim 9 further comprising the steps of:

introducing an end of an instrument into an interface between an exterior of the enveloping member and surrounding tissue; and performing a surgical procedure in the interface with the instrument.

11. The method of claim 1 further comprising the steps of:

providing a handle having an internal compartment and operatively connected to the enveloping member; and storing the enveloping member in the collapsed position in the compartment.

12. A method for isolating at least a portion of an organ within an enveloping sleeve in an interior of a patient's body, the enveloping sleeve having walls of flexible material with an inside surface and an outside surface, the enveloping sleeve being capable of movement between an inside-out condition and a right side-out condition, the enveloping sleeve storable in a handle coupled to the enveloping sleeve in the inside-out condition, the method comprising the steps of:

making an incision in the patient's body, thereby providing access to a portion of the organ in the interior of the patient's body;

positioning the enveloping sleeve in the inside-out condition proximate to the portion of the organ;

maintaining the handle in a substantially fixed position relative to the organ;

moving the enveloping sleeve toward the right side-out position from the inside-out position, thereby causing the enveloping sleeve to unfold in 360 degrees distally around at least a portion of the organ, thereby isolating at least a portion of the organ within the enveloping sleeve and isolated from surrounding tissues.

13. The method of claim 12 wherein the moving step includes the step of applying a fluid pressure to the inside surface of the walls of the enveloping sleeve, thereby causing the enveloping sleeve to unfold in 360 degrees distally around at least a portion of the organ.

14. A method for isolating at least a portion of an anatomic structure in an interior of a patient's body within an enveloping structure, the enveloping structure having walls of flexible material surrounding an inflation chamber, the enveloping structure capable of deployment between a non-deployed position and a deployed position, in the non-deployed position the inflation chamber being collapsed with the enveloping structure foldably stored in a handle coupled to the enveloping sleeve, in the deployed position the inflation chamber expanded by a fluid medium with the enveloping structure being unfoldably deployed distally from the handle, the walls of the enveloping structure defining an axial lumen extending through the enveloping structure, the axial lumen being exterior to the walls surrounding the inflation chamber, the method comprising the steps of:

positioning at least a portion of the enveloping structure in the non-deployed position in the interior of the patient's body whereby the axial lumen is proximate to the anatomic structure in the interior of the patient's body;

maintaining the handle in a substantially fixed position relative to the anatomic structure;

introducing a fluid medium into the inflation chamber, thereby causing the enveloping structure to move toward the deployed position from the non-deployed position, wherein such distal deployment causes the enveloping structure to unfold around at least a portion of the anatomic structure, thereby isolating at least a portion of the anatomic structure in the axial lumen.

15. The method of claim 14 wherein the positioning step is preceded by the step of dividing the anatomic structure to provide an end portion of the anatomic structure.

16. The method of claim 14 wherein the introducing step includes the step of unfolding the enveloping structure distally by turning to a right side-out condition from an inside-out condition.

17. The method of claim 14 wherein the introducing step includes the step of unfolding the enveloping structure distally by unrolling.

18. The method of claim 14 wherein the introducing step is preceded by the step of advancing an instrument through the axial lumen of the enveloping structure to positionally maintain the portion of the anatomic structure.

19. The method of claim 14 wherein the introducing step is preceded by the step of disposing an instrument in an interior lumen in the anatomic structure.

20. The method of claim 19 wherein the instrument is maintainable in one of a flexible, semi-rigid or rigid configuration.

21. The method of claim 14 further comprising the step of viewing through a transparent wall of the enveloping structure particular anatomic structures exterior of the enveloping structure.

22. The method of claim 14 further comprising the steps of:

advancing a working end of an instrument into an interface between an exterior of the enveloping structure and surrounding tissues; and performing a surgical procedure in the interface with the working end of the instrument.

23. The method of claim 14 further comprising the step of dividing the anatomic structure beyond a distal end of the enveloping structure, thereby capturing a portion of the anatomic structure within the axial lumen.

24. The method of claim 23 further comprising the step of withdrawing the enveloping structure from the patient's body with the portion of the anatomic structure captured therein.

25. The method of claim 14 wherein the introducing step includes the step of applying generally radially-directed inward forces on the walls around the axial lumen with the fluid medium, thereby pressing the walls onto the anatomic structure disposed therein and thereby maintaining the anatomic structure in its original position without displacement.

26. A method for removing a portion of an elongate vessel having a least one branch vessel from an interior of a patient's body utilizing a device having an enveloping structure with walls of substantially transparent flexible material surrounding an inflation chamber, the enveloping structure being capable of deployment between a non-deployed position and a deployed position, in the non-deployed position the inflation chamber being collapsed with the enveloping structure foldably stored in a handle coupled to the enveloping structure, in the deployed position the inflation chamber being expanded by a fluid medium with the enveloping structure being unfoldably deployed distally from the handle, the enveloping structure capable of accommodating viewing means within the inflation chamber, the walls of the enveloping structure defining an axial lumen extending through the enveloping structure, the axial lumen being exterior to the walls surrounding the inflation chamber, the method comprising the steps of:

making a first incision in a first location in the patient's body, thereby providing access to a first portion of the elongate vessel in the interior of the patient's body;

making a second incision in a second location in the patient's body, thereby providing access to a second portion of the vessel;

advancing an elongate probe along an exterior of the elongate vessel, thereby dissecting a pathway between the first and second locations along side the vessel;

dividing the vessel at at least one of the first and second locations, thereby providing one of a first and second end portions of the vessel;

positioning the enveloping structure in the non-deployed position in one of the first and second incisions, whereby the axial lumen is proximate to one of the first and second end portions of the vessel;

introducing a fluid medium into the inflation chamber, thereby moving the enveloping structure toward the deployed position from the non-deployed position, wherein distal deployment causes the enveloping structure to unfold around one of the first and second end portions of the vessel, thereby isolating at least a portion of the vessel in the axial lumen;

endoscopically viewing the at least one branch vessel through the pathway;

guiding under endoscopic viewing an instrument though one of the first and second incisions to a location of the at least one branch vessel;

dividing the at least one branch vessel with the instrument; and withdrawing the enveloping structure from the patient's body through one of the first and second incisions with a portion of the vessel captured therein.

27. The method of claim 26 wherein the endoscopically viewing is through the transparent walls.

28. The method of claim 26 wherein the endoscopically viewing is along an interface between the enveloping structure and surrounding tissues.

29. The method of claim 26 wherein the accessory instrument is guided into the patient's body along an interface between the enveloping structure and surrounding tissues.

* * * * *